US00PP29662P2

(12) United States Plant Patent
Krassenburg

(10) Patent No.: US PP29,662 P2
(45) Date of Patent: Sep. 11, 2018

(54) ***DAHLIA* PLANT NAMED 'BALDENREK'**

(50) Latin Name: *Dahlia variabilis*
Varietal Denomination: Baldenrek

(71) Applicant: Ball Horticultural Company, West Chicago, IL (US)

(72) Inventor: Jolanda Krassenburg, Enkhuizen (NL)

(73) Assignee: Ball Horticultural Company, West Chicago, IL (US)

( * ) Notice: Subject to any disclaimer, the term of this patent is extended or adjusted under 35 U.S.C. 154(b) by 34 days.

(21) Appl. No.: 15/530,928

(22) Filed: Mar. 24, 2017

(51) Int. Cl.
*A01H 5/02* (2018.01)

(52) U.S. Cl.
USPC ..... Plt./321

(58) Field of Classification Search
USPC ..... Plt./263.1, 321
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Dahlia* plant named 'Baldenrek', characterized by its double-type, dark red-colored inflorescences, medium green-colored foliage, and vigorous, upright-mounded growth habit, is disclosed.

1 Drawing Sheet

Latin name of genus and species of plant claimed: *Dahlia variabilis*.

Variety denomination: 'Baldenrek'.

BACKGROUND OF THE INVENTION

The present invention relates to a new and distinct cultivar of *Dahlia* plant botanically known as *Dahlia variabilis* and hereinafter referred to by the cultivar name 'Baldenrek'.

The new cultivar originated in a controlled breeding program in Venhuizen, the Netherlands during August 2011. The objective of the breeding program was the development of *Dahlia* cultivars that are freely flowering with large flowers and a vigorous, upright-mounded growth habit.

The new *Dahlia* cultivar is the result of cross-pollination. The female (seed) parent of the new cultivar is the proprietary *Dahlia variabilis* breeding selection coded 10302, not patented, characterized by its anemone-type, medium pink-colored flowers, medium green-colored foliage, and moderately vigorous, upright-mounded growth habit. The male (pollen) parent of the new cultivar is the proprietary *Dahlia variabilis* breeding selection coded 10154, not patented, characterized by its double-type, dark red-colored flowers, medium green-colored foliage, and moderately vigorous, compact-mounded growth habit. The new cultivar was discovered and selected as a single flowering plant within the progeny of the above stated cross-pollination during August 2012 in a controlled environment in Venhuizen, the Netherlands.

Asexual reproduction of the new cultivar by terminal stem cuttings since August 2012 in Venhuizen, the Netherlands and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baldenrek' as a new and distinct cultivar of *Dahlia* plant:

1. Double-type, dark red-colored inflorescences;
2. Medium green-colored foliage; and
3. Vigorous, upright-mounded growth habit.

Plants of the new cultivar differ from plants of the female parent primarily in flower color, flower-type, and growth vigor. Plants of the new cultivar differ from plants of the male parent primarily in having more branches per plant, more ray florets per inflorescence, and increased growth vigor.

Of the many commercially available *Dahlia* cultivars, the most similar in comparison to the new cultivar is DAHLINOVA HYPNOTICA Red 'Fidahhypre' U.S. Plant Pat. No. 21,252. However, in comparison, plants of the new cultivar differ from plants of 'Fidahhypre' in at least the following characteristics:

1. Plants of the new cultivar have a ray floret color that is darker red than plants of 'Fidahhypre';
2. Plants of the new cultivar have a smaller diameter inflorescences than plants of 'Fidahhypre'; and
3. Plants of the new cultivar have disc florets unlike plants of 'Fidahhypre'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldenrek'. The plants were grown in 4.5-inch pots for 11 weeks in a greenhouse in West Chicago, Ill. Plants were given one pinch one week after transplant.

DETAILED BOTANICAL DESCRIPTION

Figure 1:
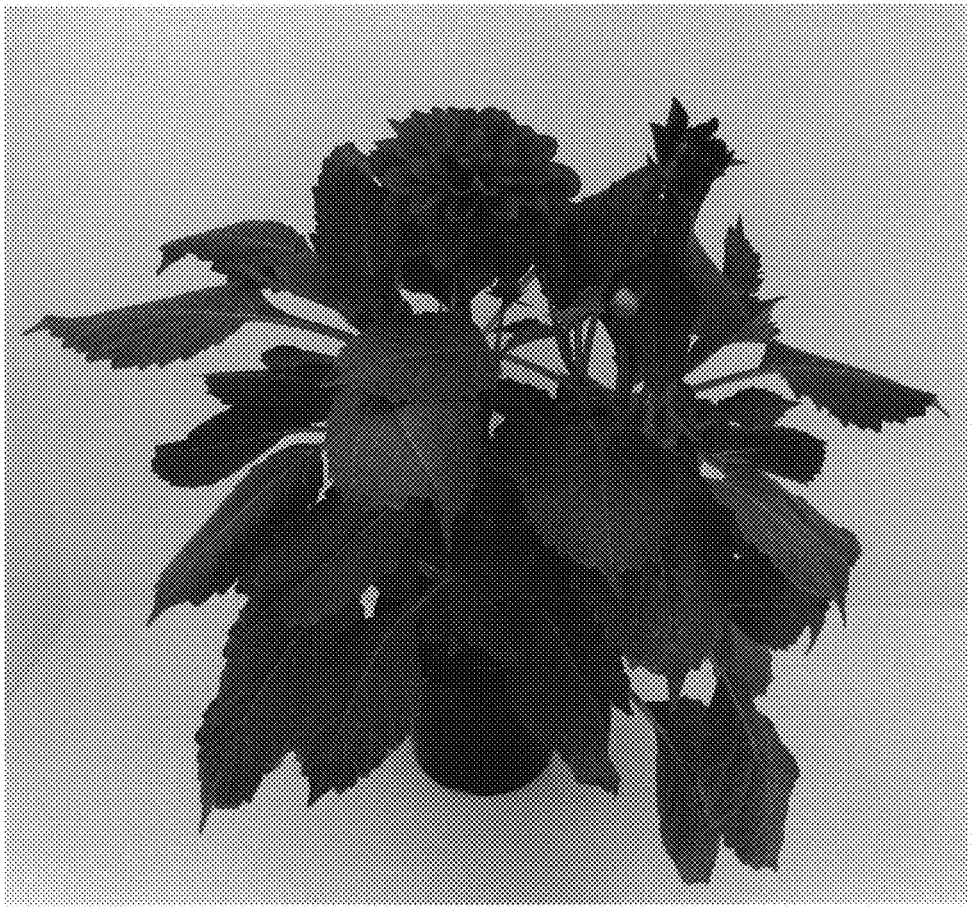
FIG. 1 illustrates a side view of the overall growth and flowering habit of 'Baldenrek'.
Figure 2:
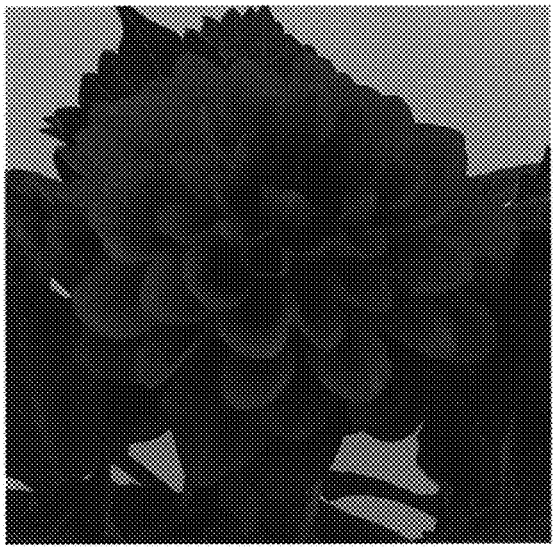
FIG. 2 illustrates a close-up view of an individual inflorescence of 'Baldenrek'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2017 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 11 weeks utilizing a soilless growth medium. Plants were given one pinch one week after transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Dahlia variabilis* cultivar Baldenrek.

Parentage:

*Female parent*.—Proprietary *Dahlia variabilis* breeding selection coded 10302, not patented.

*Male parent*.—Proprietary *Dahlia variabilis* breeding selection coded 10154, not patented.

Propagation:

*Type cutting*.—Terminal stem.

*Time to initiate roots*.—Approximately 7 to 10 days.

*Time to produce a rooted cutting*.—Approximately 21 to 28 days.

*Root description*.—Fine, fibrous.

*Rooting habit*.—Freely branching.

*Tuber formation*.—Will form under short day conditions of at least 13 to 14 hours of darkness.

Plant description:

*Commercial crop time*.—Approximately 6 to 8 weeks from a rooted cutting to finish in a 15 cm pot.

*Growth habit and general appearance*.—Vigorous, upright-mounded.

*Size*.—Height: Approximately 31.0 cm. Width: Approximately 37.0 cm.

*Branch*.—Quantity of main branches per plant: Approximately 2. Strength: Moderately strong. Length to base of peduncle: Approximately 12.5 cm. Diameter at central internode: Approximately 8.0 mm. Texture: Glabrous. Color: 144A. Length of central internode: Approximately 2.3 cm.

Foliage description:

*General description*.—Quantity of leaves per lateral branch: Approximately 8. Type: Simple and trifoliate. Fragrance: None detected. Arrangement: Opposite. Aspect: Petiole is acute angle to stem; blade is somewhat perpendicular to stem. Shape of leaf and leaflet: Elliptic. Margin of leaf and leaflet: Widely serrate. Apex of leaf and leaflet: Acute. Base of leaf and leaflet: Broadly attenuate to rounded. Venation pattern: Pinnate.

*Simple leaf*.—Length: Approximately 9.0 cm. Width: Approximately 6.0 cm. Texture of upper and lower surfaces: Sparsely pubescent, ciliate. Color of upper surface when first and fully open: Closest to but darker than NN137A with venation of 147C. Color of lower surface when first and fully open: Closest to 191B with venation of 147C. Length of petiole: Approximately 4.5 cm. Diameter of petiole: Approximately 4.0 mm. Texture of upper and lower surfaces of petiole: Glabrous. Color of upper and lower surfaces of petiole: 147C.

*Mature trifoliate leaf*.—Length of mature trifoliate leaf: Approximately 11.5 cm. Width of mature trifoliate leaf: Approximately 12.5 cm. Length of terminal leaflet: Approximately 8.0 cm. Width of terminal leaflet: Approximately 5.0 cm. Length of lateral leaflet: Approximately 6.0 cm. Width of lateral leaflet: Approximately 3.5 cm. Texture of upper and lower surfaces: Sparsely pubescent, ciliate. Color of upper surface when first and fully open: Closest to but darker than NN137A with venation of 147C and small spot of 187A at base of lateral leaflets. Color of lower surface when first and fully open: Closest to 191B with venation of 147C. Length of petiole of mature trifoliate leaf: Approximately 6.0 cm. Diameter of petiole of mature trifoliate leaf: Approximately 4.0 mm. Texture of upper and lower surfaces of petiole of mature trifoliate leaf: Glabrous. Color of upper and lower surfaces of petiole of mature trifoliate leaf: 147C. Length of rachis: Approximately 2.0 cm. Diameter of rachis: Approximately 2.0 mm. Texture of upper and lower surfaces of rachis: Glabrous. Color of upper and lower surfaces of rachis: 147C.

Flowering description:

*Flowering habit*.—'Baldenrek' is freely flowering under outdoor growing conditions with substantially continuous blooming from spring through autumn and year round in the greenhouse environment.

*Lastingness of individual inflorescence on the plant*.—Approximately 2 weeks.

Inflorescence description:

*General description*.—Type: Composite, double, persistent. Aspect: Facing upward and outward. Arrangement: Terminal, arising from leaf axils on strong peduncles positioned over the foliage. Disc and ray florets arranged acropetally on a capitulum. Quantity per plant: Approximately 2. Fragrance: Slight. Shape: Hemispherical. Inflorescence diameter: Approximately 7.5 cm. Inflorescence depth: Approximately 4.0 cm. Disc diameter: Approximately 6.0 mm. Receptacle diameter at base: Approximately 1.0 cm. Receptacle depth: Approximately 4.0 mm. Receptacle color: 150C to 150D.

*Peduncle*.—Strength: Strong. Aspect: Erect. Length: Approximately 11.5 cm. Diameter: Approximately 4.0 mm. Texture: Glabrous. Color: 146B with a faint overlay of 187A.

*Bud*.—Rate of bud opening: Generally takes 2 weeks for bud to progress from first color to fully open flower. Quantity per plant: Approximately 2.

*Bud just before opening*.—Shape: Globular. Diameter: Approximately 1.2 cm. Texture: Glabrous. Color: Outer surface of the phyllaries 154C with 144A at base, petals of 53A.

*Ray florets*.—Quantity per inflorescence: Approximately 80. Arrangement: Imbricate, in multiple whorls. Aspect: Cupped. Shape: Elliptic. Margin: Entire. Apex: Broadly acute. Base: Fused into a short tube. Appearance: Velvety. Length: Approximately 3.4 cm. Width: Approximately 1.6 cm. Texture of upper surface: Glabrous. Texture of lower surface: Sparsely pubescent, ribbed. Color of upper surface when first and fully open: Closest to but darker than 53A. Color of lower surface when first and fully open: 53A with stripes of 51C and base of 155A.

*Disc florets*.—Quantity per inflorescence: Approximately 20. Arrangement: Massed in center of inflorescence. Aspect: Erect. Shape: Tubular. Margin: Entire. Apex: 5 acute tips. Base: Fused. Length: Approximately 1.2 cm. Diameter at apex: Approximately 2.0 mm. Diameter at base: Approximately 1.0 mm. Texture: Glabrous. Color when fully open: 17A, translucent with base of 155D.

*Outer phyllaries*.—Quantity: 5 to 6. Aspect: Flat. Shape: Rhombic. Margin: Entire. Apex: Acute. Base: Truncate. Length: Approximately 1.2 cm. Width: Approximately 5.0 mm. Texture of upper and lower surfaces: Glabrous. Color of upper surface: 137B. Color of lower surface: 137A.

*Inner phyllaries*.—Quantity: Approximately 1 per floret. Shape: Linear, imbricate. Margin: Entire. Apex: Broadly acute. Base: Truncate. Length of outermost: Approximately 1.7 cm. Width of outermost: Approximately 5.0 mm. Length of innermost: Approximately 9.0 mm. Width of innermost: Approximately 2.0 mm. Texture of upper and lower surfaces: Glabrous. Color of upper and lower surfaces: 154D, translucent with 143A at base of outermost.

*Reproductive organs*.—Androecium: Disc florets. Stamen quantity: 5 per floret. Stamen length: Approximately 6.0 mm. Anther shape: Linear. Anther length: Approximately 3.0 mm. Anther color: 21B. Pollen amount: Abundant. Pollen color: 21A. Gynoecium: Disc florets. Pistil length: Approximately 1.2 cm. Stigma shape: 2 branched. Stigma length: Approximately 2.0 mm. Stigma color: 21A. Style length: Approximately 8.0 mm. Style color: 1A. Ovary length: Approximately 2.0 mm. Ovary color: 155D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldenrek', substantially as herein illustrated and described.

* * * * *